United States Patent [19]

Coopersmith et al.

[11] 4,125,549
[45] Nov. 14, 1978

[54] PROCESS FOR THE MANUFACTURE OF COSMETIC QUALITY ISOOCTYL NEODECANOATE

[75] Inventors: Myron Coopersmith, Livingston, N.J.; Leo Z. Jasion, deceased, late of Roselle, N.J., by Florence F. Jasion, Administratrix

[73] Assignee: Exxon Research & Engineering Co., Linden, N.J.

[21] Appl. No.: 834,770

[22] Filed: Sep. 19, 1977

Related U.S. Application Data

[63] Continuation of Ser. No. 685,346, May 12, 1976, abandoned, which is a continuation-in-part of Ser. No. 614,787, Sep. 19, 1975, abandoned, which is a continuation of Ser. No. 359,422, May 11, 1973, abandoned.

[51] Int. Cl.$^2$ .................. C11B 3/06; A61K 7/025
[52] U.S. Cl. ................... 260/425; 260/428; 424/64; 424/365
[58] Field of Search .............. 260/410.9 R, 420, 425, 260/426, 428, 428.5; 424/365, 64

[56] References Cited

U.S. PATENT DOCUMENTS 3,035,987  5/1962  Weitzel ................ 260/410.9 R
3,590,059  6/1971  Velan ..................... 260/423

OTHER PUBLICATIONS

Coopersmith et al, I & EC Product Research and Development, vol. 5, No. 1, Mar. 1966, pp. 45–49.
Rini, The Journal of the Am. Oil Chemists Society, vol. 37, pp. 512-20, Oct. 1960.

Primary Examiner—John Niebling
Attorney, Agent, or Firm—C. Leon Kim

[57] ABSTRACT

Cosmetic quality isooctyl neodecanoate is manufactured by contacting an alcohol mixture containing a major amount of isooctyl alcohol with neodecanoic acid in the presence of an acid catalyst and at a temperature of from about 160° C. to about 230° C. to yield a crude ester product; treating the crude ester product at a temperature of from about 50° C. to about 150° C. with a basic material to reduce the sulfur level of said crude ester product to less than about 20 ppm; distilling the product thus recovered at a temperature in the range of about 150° C. to about 185° C. and at a pressure in the range of from about 1 to about 20 mm Hg; steam stripping the distilled product in the presence of an antioxidant to deodorize; and recovering a yield of cosmetic quality isooctyl neodecanoate. The purified ester product is useful in cosmetic formulations.

13 Claims, No Drawings 4,125,549

PROCESS FOR THE MANUFACTURE OF COSMETIC QUALITY ISOOCTYL NEODECANOATE

CROSS-REFERENCE TO RELATED APPLICATIONS

This is a continuation of application Ser. No. 685,346, filed May 12, 1976, abandoned, which in turn is a continuation-in-part of U.S. Ser. No. 614,787, filed Sept. 19, 1975, abandoned, which is in turn a continuation of U.S. Ser. No. 359,422, filed May 11, 1973, abandoned.

BACKGROUND OF THE INVENTION

1. Field of the Invention

The present invention relates to a process for the preparation of cosmetic quality isooctyl neodecanoate. The product, a complex mixture of esters, is odorless, colorless, has good emolliency properties, and finds utility as a suitable replacement for the costly and diminishing supply of isopropyl myristate.

2. Description of the Prior Art

Neoacids, i.e., trialkyl acetic acids, are difficult to esterify by conventional techniques. This difficulty has been described in Hind, "J. Physical Organic Chemistry," pages 266–276, McGraw Hill, New York, 1956; and also in Newman, M. S., "Steric Effects in Organic Chemistry," Wiley, New York, 1956. Because of this difficulty and the concomitant requirement of rigorous techniques for esterifying such acids, the esters of neoacids have never been seriously considered as useful cosmetic oil materials.

As isooctyl neodecanoate can be an effective replacement for isopropyl myristate, an efficient, high yield process for the commercial preparation of this ester is herein provided.

SUMMARY OF THE INVENTION

In accordance with the present invention, cosmetic quality isooctyl neodecanoate can be produced in an economically feasible quantity. The process comprises: (a) contacting an alcohol mixture, containing in a major amount isooctyl alcohol, with neodecanoic acid in the presence of a catalyst and at a temperature of from about 160° C. to about 230° C. to yield a crude ester product; (b) treating said crude ester product at a temperature of from about 50° C. to about 100° C. with a basic material to reduce the sulfur level of said crude ester product to less than about 20 ppm; (c) distilling the product recovered in step (b) above at a temperature in the range of from about 150° C. to about 185° C. and at a pressure in the range of from about 1 to about 20 mm Hg; (d) steam stripping said distilled ester product at a temperature in the range of from about 50° C. to about 115° C. in the presence of an antioxidant to completely deodorize; and (e) recovering a yield of cosmetic quality isooctyl neodecanoate (IOND).

The present process is applicable to the manufacture of a wide variety of branched chain esters wherein branched chain alcohols are reacted with neoacids; preferably, however, the process is directed to the manufacture of cosmetic quality isooctyl neodecanoate. The description of the process will be directed to the preferred embodiment but is equally applicable to a process wherein neoacids such as neopentanoic, neoheptanoic and neotridecanoic acids may be reacted with branched chain alcohols having from 3 to 24 carbon atoms. Non-limiting representative examples of the branched chain alcohols that can be employed in the manufacture of cosmetic quality esters include isopropyl, isobutyl, isohexyl, isodecyl and hexadecyl alcohols. In the operation of the present process, in its preferred embodiment, as mentioned above, isooctyl neodecanoate is the material to be produced.

The starting materials are commercially available isooctyl alcohol which has as a typical composition: 80 wt. % dimethyl-1-hexanols, 15 wt. % methyl-1-heptanols and 5% other homologous primary alcohols. The neodecanoic acid employed is also a commercial material and is a mixture of $C_{10}$ trialkyl acetic acids having a typical alpha carbon atom configuration such as 31% 2,2-dimethyl, 67% 2-methyl-2-higher alkyl and 2% 2,2-di-higher alkyl. The product isooctyl neodecanoate is therefore a complex ester mixture of the above reactants.

The first step of the process concerns contacting the alcohol with the acid in the presence of the catalyst. The catalyst to be employed typically is sulfuric acid having a concentration range of from 0.1 to 3.0 wt. %, preferably 1 wt. % based on total charge. However, other acids such as p-toluene sulfonic, hydrochloric, hydrofluoric, etc., may be employed. This esterification reaction is carried out at a temperature of from about 160° C. to about 230° C., more preferably from 175° to 220° C., most preferably from 185° to 210° C. The preferred mole ratio for near 100% conversion based on acid feed is 1.10 moles of the alcohol per mole of acid. However, the esterification reaction may be carried out with from 1.0 to 5.0 moles of alcohol per mole of acid. In carrying out the esterification reaction, an entrainer such as toluene may be optionally employed to assist in removal of the water of esterification. Water can also be removed by other means known in the art such as vacuum distillation.

The crude ester product which results from the esterification reaction described above is dark and contains odor causing contaminants as well as a high level of the acid catalyst. In order to obtain a cosmetic quality ester product, therefore, a number of purification steps are employed. First, the crude ester product is neutralized with a basic material, e.g., an aqueous caustic solution or anhydrous sodium carbonate, which is commonly known as soda ash, to reduce the sulfur level to less than about 20 ppm, preferably to less than about 10 ppm, more preferably to less than about 5 ppm, and most preferably to less than about 2 ppm. This neutralization step is carried out at a temperature of from about 50° C. to about 150° C., preferably from 75° to 95° C. The amount of said basic material is in the range of from about 5 to about 20 wt. %, preferably from about 6 to about 10 wt. % and more preferably from about 7 to about 8 wt. %, based on total charge. The contact time is important and typical contact times are in the range of from about 0.1 to about 4 hours, preferably from about 0.75 to about 2 hours. Moreover, vigorous agitation is important in order to effectively remove substantially all of the sulfur.

The neutralized ester product is then distilled at a temperature in the range of from 150° C. to about 185° C. and at a pressure in the range of from about 1 to about 20 mm Hg, preferably from about 160° to 175° C. at a given pressure of about 10 mm Hg, to thereby remove a first major group of the odor causing contaminants. This first group of the odor causing contaminants comes off in the heads of the distillation column together with alcohol; and color bodies remain as the bottoms by-product. The ester product is obtained as the heart-cut portion from the fractional distillation tower. It has been discovered that this ester product still contains a second group of odor causing by-products which have a boiling range slightly lower than that of IOND but higher than that of alcohol and the first group of odorous contaminants.

This partially deodorized ester product is then further deodorized by steam stripping in the presence of an antioxidant in an amount ranging from about 10 to about 100 ppm, preferably from about 15 to about 70 ppm and more preferably from about 20 to about 40 ppm. The use of an antioxidant is essential in order to prevent the formation of a third group of odor causing compounds during the steam-stripping step wherein the second group of the odor causing contaminants are separated from the ester product. This antioxidant may be added either before or after distilling (but before steam stripping) the neutralized crude ester product. Nonlimiting representative antioxidants include citric acid, 2,6-di-t-butyl-p-cresol (hereinafter referred to as Parabar 441), 2,6-di-t-butylphenol, 4,4'-methylene-bis-2,6-di-t-butylphenol, methylene-bridged-polyalkylphenols, 2,6-di-t-butyl-α-dimethylamino-p-cresol, N,N'-di-sec-butyl-p-phenylenediamine, N,N'-diisopropyl-p-phenylenediamine, trisnonylphenylphosphite, isoindoline, alkylhydroxyphenylthiol-alkanoates, alkoxy-2,6-di-t-butyl-p-cresol-dibutyl-tin-sulfide, triazoles and the like. These antioxidants can be employed either alone or in combination. The steam stripping of the second group of odor causing contaminants, which group of contaminants having slightly lower boiling points than the desired ester product, is carried out by passing steam in an amount of about 25 weight % based on total charge through the product contained either in a kettle or in a wiped film evaporator at a temperature in the range of from about 50° C. to about 120° C., preferably from about 90° C. to 115° C. for about 2 to 5 hours. The final color of the ester product is from 10 to 15 on the Platinum Cobalt color scale. After steam stripping, cosmetic quality isooctyl neodecanoate is then recovered as final product.

The isooctyl neodecanoate as produced above is a colorless, odorless compound which is suitable as a cosmetic oil. In extensive testing in cosmetic formulations, isooctyl neodecanoate has been found to be comparable and in some cases superior to the widely used isopropyl myristate (IPM). Tables I to IV compare the physical and formulation properties of IOND and IPM.

TABLE I
COMPARISON OF PROPERTIES - IOND VS. IPM

| Typical Properties | IOND | IPM |
|---|---|---|
| Freezing Point, ° F. | <−35 | +36 |
| Viscosity cps, 77° F. | 5.9 | 5.6 |
| Viscosity cps, 100° F. | 4.1 | 3.6 |
| Alkaline Hydrolysis at 25° C. (% hydrolyzed) | | |
| 2 hours | 0 | 22 |
| 4 hours | 0 | 48 |
| 6 hours | 0 | 72 |
| Miscibility | | |
| Mineral Oil | S | S |
| Castor Oil | S | S |
| Propylene Glycol | I | I |
| Ethanol, Anhydrous | S | S |

S = Soluble, inifinite miscibility.
I = Insoluble.

TABLE II
COMPARISON OF SOLIDS SOLUBILITY - IOND VS. IPM

| | Weight Percent | |
|---|---|---|
| | IOND | IPM |
| Beeswax | 0.6 | 0.3 |
| Ceresin Wax | <0.1 | <0.1 |
| Paraffin Wax | 2.8 | 2.7 |
| Candelilla Wax | 0.6 | 0.5 |
| Carnauba Wax | <0.1 | <0.1 |
| Cetyl Alcohol | 9 | 10 |
| Lanolin | 17 | 15 |
| Stearic Acid | 6.5 | 8.5 |
| Glycerol Monostearate, Pure | 1.2 | 1.7 |

TABLE III
COMPARISON IN COSMETIC FORMULATIONS - IOND VS. IPM

| Product | Example | Performance Differences | Significance |
|---|---|---|---|
| Gels | Hair Groom | IOND formed clear gel (IPM formed clear very viscous liquid after two days). | Expands use for IOND. Esters do not generally give clear gels. |
| Creams and Lotions | Cold Cream Cleansing Cream All Purpose Lotion | No Significant difference | IOND can be substituted for IPM in creams and lotions. |
| Adsorption Base Emulsions | Can be utilized in W/O creams | IOND more easily emulsifiable and more stable than IPM | Expands use for IOND. Esters do not generally form good adsorption base emulsions. |
| Make-up | Blusher Mascara Foundation Make-up Liquid Make-up | No significant difference | IOND can be substituted for IPM in make-up formulations. |
| Specialties | Preshave Lotion Hair Spray Bath Oil Alcohol Soluble Antiperspirant | IOND samples were liquid at −6° F (IPM samples were frozen) | IOND provides fewer packaging problems at low temperatures. |

TABLE IV
COMPARISON IN AEROSOL ANTIPERSPIRANTS - IOND VS. IPM

| | Weight Percent | |
|---|---|---|
| | IOND | IPM |
| Isooctyl Neodecanoate | 6.0 | — |
| Isopropyl Myristate | — | 6.0 |
| Cab-O-Sil M-5* | 0.5 | 0.5 |
| Micro Dry, Impalpable** | 3.0 | 3.0 |
| Propellants 11/12 (65:35) | 90.5 | 90.5 |
| Number of Cans Tested | 10 | 10 |
| Ease of Redispersibility (#180° rotations) | | |
| 1 day | 3 | 4 |
| 3 days | 3 | 3 |
| 7 days | 3 | 3 |
| 10  30 days | 3 | 3 |
| Valve Clogging (Percent Sprayed) | 80-100 | 80-100 |

*Fumed Silica, Cabot
**Aluminum Chlorohydrate, Reheis

Because of these properties set forth above, IOND may be used in many different kinds of cosmetic formulations. Typical formulations exhibited here in the way of illustration and not to be construed as limiting are as follows.

| HAIR GROOM | |
|---|---|
| Oil Phase | Weight Percent |
| Isooctyl Neodecanoate | 19.60 |
| Mineral Oil | 4.90 |
| Anhydrous Lanolin | 1.90 |
| Ethoxylan 100[1] | 1.90 |
| Arlacel 80[2] | 2.60 |
| Tween 80[3] | 5.30 |
| Atlas G-1726[4] | 3.90 |
| Ucon 50 HB-2000[5] | 4.80 |
| Water Phase | |
| Distilled Water | 43.00 |
| Carbopol 960[6] | 0.40 |
| Ethosperse 12 LA[7] | 9.80 |
| Propylene Glycol | 1.90 |
| | 100.00 |

[1] Ethoxylated Lanolin, Malmstrom Chem.
[2] Sorbitan Monooleate, ICI America
[3] Polyoxyethylene sorbitan monooleate, ICI America.
[4] Polyoxyethylene sorbitol beeswax derivative, ICI America.
[5] W. S. Polyalkylene glycol w/2000 SSU vis, Union Carbide
[6] Carboxy vinyl copolymer, Goodrich
[7] Polyoxyethylene 12 lauryl alcohol, Glycol Chem.

The Carbopol is added to the water at room temperature with agitation. The Ethosperse and Propylene Glycol are then added to the thin gel and the mixture heated with stirring to 75° C. The ingredients of the oil phase are combined and heated to 75° C. with stirring. The oil phase is added to the water phase at 75° C. and stirring is continued until room temperature. Perfume oil, as desired, is added at 35° C.

| COLD CREAM | |
|---|---|
| Oil Phase | Weight Percent |
| Isooctyl Neodecanoate | 8.15 |
| Mineral Oil | 32.25 |
| Beeswax | 15.30 |
| Petrolatum | 3.30 |
| Propyl p-Hydroxybenzoate | 0.10 |

| Water Phase | Weight Percent |
|---|---|
| Distilled Water | 39.50 |
| Borax | 1.20 |
| Methyl p-Hydroxybenzoate | 0.20 |
| | 100.00 |

The oil and water phases are heated separately to 70° C. The oil phase is then added to the water phase with careful agitation to prevent entrainment of air. When the emulsion is well formed, the mixture is allowed to cool to room temperature with constant stirring. Perfume oil, as desired, is added at 35° C.

MOISTURIZING LOTION

Solution A

In 97.50 parts by weight of distilled water disperse 1.25 parts by weight of Carbopol 9341 with agitation. After solution has been effected add 1.25 parts by weight of 10% aq. diisopropanolamine.

| Oil Phase | Weight Percent |
|---|---|
| Mineral Oil | 20.0 |
| Isooctyl Neodecanoate | 6.0 |
| Anhydrous Lanoline | 1.0 |
| Arlacel 80[2] | 2.6 |
| Tween 80[3] | 5.5 |
| Water Phase | |
| Solution B | 20.0 |

| -continued | |
|---|---|
| Propylene Glycol | 2.2 |
| Methyl p-Hydroxybenzoate | 0.1 |
| Distilled Water | 42.4 |
| Perfume Oil | 0.2 |
| | 100.00 |

[2] Sorbitan monooleate, ICI America
[3] Polyoxyethylene sorbitan monooleate, ICI America The oil and water phases are heated separately to 75° C. The oil phase is then added to the water phase with careful agitation. The mixture is allowed to cool to room temperature with constant stirring. Perfume is added at 35° C.

| MEN'S HAIR DRESSING | Volume Percent |
|---|---|
| Isooctyl Neodecanoate | 18.0 |
| Ethyl Alcohol (SDA-40) | 68.0 |
| Ucon LB-1715 (Union Carbide Chemicals Co.)[8] | 7.0 |
| Distilled Water | 6.0 |
| Perfume Oil | 1.0 |
| | 100.00 |

[8] W. insol. polyalkylene glycol 1715 SSU vis.; Union Carbide.

The perfume oil, IOND and Ucon LB-1715 are added to the ethyl alcohol in that order. The water is added last. The mixture is chilled and filtered.

| SPREADING BATH OIL | Weight Percent |
|---|---|
| Isooctyl Neodecanoate | 76.0 |
| Robane[9] | 10.0 |
| Ethylan[10] | 5.0 |
| Arlatone T[11] | 1.0 |
| Perfume Oil | 8.0 |
| | 100.0 |

[9] Squalane, Robeco Co.
[10] Alc. sol. lanolin, Robinson-Wagner.
[11] Polyoxyethylene polyol fatty acid ester, ICI America.

Combine ingredients and package. Color, as desired, may be added.

DESCRIPTION OF THE PREFERRED EMBODIMENTS

The invention will be further understood by reference to the following examples.

EXAMPLE 1

Example 1 describes a typical processing scheme for the preparation of IOND.

| PROCESS SCHEME FOR IOND | |
|---|---|
| 1. Synthesis | |
| Mole Ratio Isooctyl Alcohol/Neo Decanoic Acid | 1.25 |
| $H_2SO_4$, Wt. % based on total charge | 1.0 |
| Temperature, ° C. | 200 |
| Pressure, mm Hg | 400–600 |
| Time, hrs. to 98% conversion after reaction temperature reached | ~4 |
| Comment: Control pressure to give maximum boilup rate for rapid water removal. Follow conversion by titration for residual acid. | |
| Equipment: Agitated kettle with vacuum system and facilities for condensing and separating alcohol and water taken overhead prior to return of alcohol to synthesis mixture. | |
| 2. Neutralization | |
| Light Soda Ash, Wt. % | 8.0 |
| Temperature, ° C. | 150 |
| Pressure, mm Hg | 760 |
| Time, hrs. | 1.0 |
| Water Addition, Wt. % | 30 |
| Comment: Add light soda ash slowly and maintain vigor- | |

PROCESS SCHEME FOR IOND -continued ous agitation. Add water at 150° C. with agitation; temperature will drop to about 95° C. Let alkaline layer settle and discard.

3. Water Wash (repeated twice)

| | |
|---|---|
| Temperature, ° C. | 95 |
| Mixing Time, hrs. | 1.0 |
| Settling Time (estimated), hrs. | 1.0 |

Comment: If product is not neutral, repeat wash.

4. Distillation (two steps)

A. Alcohol Removal

| | |
|---|---|
| Pressure, mm Hg | 20 |
| Reflux Ratio | 3/1 |
| Plates | 10 |
| Overhead Temperature, ° C. | 154 |
| Bottoms Temperature (estimated), ° C. | 165 |

Comment: Recovered alcohol is discarded.

B. Product

| | |
|---|---|
| Pressure, mm Hg | 10 |
| Reflux Ratio | 3/1 |
| Plates | 10 |
| Overhead Temperature (estimated), ° C. | 168 |

Comment: The odor causing components which remain after this step boil below IOND and above isooctyl alcohol. Product distillation is a continuation of the alcohol removal.

5. Steam Stripping (use either alternate A or B)

A. Steam Stripping in Kettle

| | |
|---|---|
| Antioxidant | |
| Parabar 441, ppm | 20 |
| Citric Acid (50% solution in ethanol), ppm | 20 |
| Steam, Wt. % | 25 |
| Temperature, ° C. | 110 |
| Time until odorless, hrs. | 3 |

Comment: Good agitation required. Thermal exposure should be minimized. A final nitrogen sparge will be required to remove traces of water.

B. Steam Stripping in Wiped Film Evaporator

| | |
|---|---|
| Antioxidant | same as above |
| Steam, Wt. % | 5 |
| Pressure, mm Hg | 10 |
| Bottoms Temperature, ° C. | 110 |
| Estimated Feed Rate (lbs. feed/hr/ft² H.T. surface) | 50-75 |

Comment: Remove trace odor by treating with countercurrent nitrogen as stripping gas at room temperature and 5-10 mm Hg.

6. Product Quality

| | |
|---|---|
| Odor | Odorless |
| Color, Pt/Co | 10-15 |
| Acidity, Wt. % as acetic acid | 0.01 |
| Hydroxyl Number, mg KOH/g | 2 |
| Sulfur, ppm | 1 |

Comment: Treat with 0.5 wt. % Nuchar C-190-N at room temperature if color specification not met. Filter through celite.

EXAMPLE 2

Example 2 is designed to demonstrate the critical impact of the sulfur content remaining in the ester product after the neutralization step upon the quality of the final IOND product.

Four experiments were run in accordance with the procedure described in Example 1 except certain modifications in the neutralization step. Four batches of approximately 300 cc. crude ester product were neutralized respectively with aqueous caustic solution in amounts specified below.

| | Run (a) | Run (b) | Run (c) | Run (d) |
|---|---|---|---|---|
| Amount of crude ester product, cc. | 300 | 300 | 300 | 300 |
| Aq. sodium hydroxide, wt. % | 10 | 10 | 20 | 20 |
| Contact time, hrs. | 1 | 2 | 1 | 1 |

-continued

| | Run (a) | Run (b) | Run (c) | Run (d) |
|---|---|---|---|---|
| Final contact temp., ° C. | 95 | 95 | 95 | 95 |
| Sulfur level, ppm | 23 | 9 | 10 | 2 |
| Quality of the final IOND product | odor | odorless | odorless | odorless |

Based on the above data, it can be seen that it is necessary to reduce the sulfur level to at least less than 23 ppm in order to obtain a cosmetic quality IOND product.

EXAMPLE 3

Example 3 is intended to illustrate the criticality of employing an antioxidant in preventing the formation of a third group of odor causing contaminants during the steam-stripping step.

| | Run(1) | Run(2) | Run(3) |
|---|---|---|---|
| Weight ratio of steam to total charge | 50/200 | 40/170 | 40/130 |
| Stripping time, hrs. | 5 | 6 | 2 |
| Stripping temp., ° C. | 108 | 110 | 115 |
| Stripping pressure, mm Hg | 80 | 80 | 75 |
| Antioxidant used, ppm | none | none | 40(50% citric acid/50% Parabar 441) |
| Quality of the final product | odor | odor | odorless |

The above data shows that the formation of the third group of odor causing by-products may not be avoided even with the employment of milder conditions, i.e. lower temperatures and lower flow rates of steam (Runs (1) and (2)) unless a certain antioxidant is employed.

What is claimed is:

1. In a process for the manufacture of cosmetic quality isooctyl neodecanoate by:
   (a) contacting isooctyl alcohol with neodecanoic acid in the presence of a catalyst selected from the group consisting of sulfuric acid and p-toluenesulphonic acid at a temperature within the range of from about 160° C. to about 230° C. to form a crude ester product;
   (b) treating said crude ester product formed in step (a) with a basic material at a temperature within the range of from about 50° C. to about 150° C.;
   (c) distilling the ester product treated in step (b) at a temperature within the range of from about 150° C. to about 185° C. and at a pressure within the range of from about 1 to about 20 mm Hg; and, thereafter,
   (d) steam stripping the ester product distilled in step (c) at a temperature within the range of from about 50° C. to about 120° C.,
   the improvement which comprises:
   (i) conducting the treatment of said crude ester product in step (b) above until the sulfur content present in said crude ester product is less than about 20 ppm; and
   (ii) carrying out the steam stripping in step (d) above in the presence of an antioxidant.

2. The process of claim 1 wherein said antioxidant employed in step (ii) is selected from the group consisting of citric acid, 2,6-di-t-butyl-p-cresol, 2,6-di-t-butyl-phenol, 4,4'-methylene-bis-2,6-di-t-butylphenol, methylene-bridged-polyalkylphenols, 2,6-di-t-butyl-α-dimethylamino-p-cresol, N,N'-di-sec-butyl-p-phenylenediamine, N,N'-diisopropyl-p-phenylenediamine, trisnonylphenylphosphite, isoindoline, alkylhydroxyphenyl-thiol-alkanoates, alkoxy-2,6-di-t-butyl-p-cresol-dibutyl-tin-sulfide and triazoles.

3. The process of claim 1 wherein the amount of said antioxidant is in the range of from about 10 to about 100 ppm.

4. The process of claim 1 wherein said basic material employed in step (b) is selected from the group consisting of aqueous sodium hydroxide and anhydrous sodium carbonate.

5. The process of claim 1 wherein the amount of said basic material employed in step (b) is in the range of from about 5 to about 20 weight percent based on the total charge.

6. In a process for the manufacture of cosmetic quality isooctyl neodecanoate by:
(a) contacting isooctyl alcohol with neodecanoic acid in the presence of from about 0.1 to about 3 weight percent based on the total charge of a catalyst selected from the group consisting of sulfuric acid and p-toluenesulphonic acid at a temperature within the range of from about 160° C. to about 230° C. to form a crude ester product;
(b) treating said crude ester product formed in step (a) with a basic material selected from the group consisting of aqueous sodium hydroxide and anhydrous sodium carbonate in an amount within the range of from about 5 to about 20 weight percent based on the total charge at a temperature within the range of from about 50° C. to about 100° C.;
(c) distilling the ester product treated in step (b) at a temperature within the range of from about 150° C. to about 185° C. and at a pressure within the range of from about 1 to 20 mm Hg; and, thereafter,
(d) steam stripping the ester product distilled in step (c) at a temperature within the range of from about 50° C. to about 120° C.,
the improvement which comprises:
(i) conducting the treatment of said crude ester product in step (b) above for a period within the range of from about 0.1 to about 4 hours in order to reduct the sulfur level of said crude ester product to less than about 20 ppm; and
(ii) carrying out the steam stripping in step (d) above in the presence of from about 10 to about 100 ppm of an antioxidant selected from the group consisting of citric acid, 2,6-di-t-butyl-p-cresol, 2,6-di-t-butyl-phenol, 4,4'-methylene-bis-2,6-di-t-butyl-phenol, methylene-bridged-polyalkylphenols, 2,6,di-t-butyl-α-dimethylamino-p-cresol, N,N'-di-sec-butyl-p-phenylenediamine, N,N'-diisopropyl-p-phenylene-diamine, trisnonylphenylphosphite, isoindoline, alkylhydroxyphenyl-thiol-alkanoates, alkoxy-2,6-di-t-butyl-p-cresol-dibutyl-tin-sulfide and triazoles to recover a cosmetic quality isooctyl neodecanoate.

7. The process of claim 6 wherein the amount of said antioxidant employed in step (d) is in the range of from about 15 to about 70 ppm.

8. The process of claim 6 wherein said antioxidant employed in step (d) is selected from the group consisting of citric acid and 2,6-di-t-butyl-p-cresol.

9. The process of claim 8 wherein said antioxidant is a mixture consisting of approximately equal parts of citric acid and 2,6-di-t-butyl-p-cresol.

10. The process of claim 6 wherein the sulfur level of the crude ester product treated in step (b) is less than about 10 ppm.

11. The process of claim 6 wherein the amount of said basic material employed in step (b) is in the range of from about 6 to about 10 weight percent based on the total charge.

12. The process of claim 11 wherein said basic material is aqueous sodium hydroxide.

13. The process of claim 11 wherein said basic material is anhydrous sodium carbonate.

* * * * *